(12) United States Patent
Malik

(10) Patent No.: US 10,905,916 B1
(45) Date of Patent: Feb. 2, 2021

(54) DEVICE FOR LOGGING EXERCISE DATA AND METHOD THEREOF

(71) Applicant: Tarun Malik, San Jose, CA (US)

(72) Inventor: Tarun Malik, San Jose, CA (US)

( * ) Notice: Subject to any disclaimer, the term of this patent is extended or adjusted under 35 U.S.C. 154(b) by 25 days.

(21) Appl. No.: 16/004,381

(22) Filed: Jun. 9, 2018

Related U.S. Application Data

(60) Provisional application No. 62/521,029, filed on Jun. 16, 2017.

(51) Int. Cl.
| | | |
|---|---|---|
| *A63B 24/00* | (2006.01) | |
| *A61B 5/1171* | (2016.01) | |
| *A63B 21/062* | (2006.01) | |
| *A63B 21/072* | (2006.01) | |

(52) U.S. Cl.
CPC ........ *A63B 24/0062* (2013.01); *A61B 5/1176* (2013.01); *A63B 21/063* (2015.10); *A63B 21/0628* (2015.10); *A63B 21/0724* (2013.01); *A63B 2220/40* (2013.01); *A63B 2220/803* (2013.01); *A63B 2220/806* (2013.01); *A63B 2220/807* (2013.01); *A63B 2220/833* (2013.01); *A63B 2220/89* (2013.01); *A63B 2225/15* (2013.01); *A63B 2225/20* (2013.01); *A63B 2225/52* (2013.01); *A63B 2225/54* (2013.01)

(58) Field of Classification Search
CPC ............ A63B 24/0062; A63B 21/0628; A63B 21/0724; A63B 2225/20; A63B 2220/803; A63B 2220/806; A63B 2220/833; A63B 2225/52; A63B 2225/15; A63B 2220/40; A63B 2220/807; A63B 2220/89; A63B 2225/54; A63B 21/063; A61B 5/1176
See application file for complete search history.

(56) References Cited

U.S. PATENT DOCUMENTS

| | | | | |
|---|---|---|---|---|
| 5,000,446 A | * | 3/1991 | Sarno | A63B 21/063 482/101 |
| 9,409,053 B1 | * | 8/2016 | Todd | G16H 40/67 |
| 9,468,793 B2 | * | 10/2016 | Salmon | A63B 21/0724 |
| 2008/0242512 A1 | * | 10/2008 | Kim | A63B 21/065 482/8 |
| 2008/0242520 A1 | * | 10/2008 | Hubbard | A63B 21/0628 482/98 |
| 2009/0227432 A1 | * | 9/2009 | Pacheco | A63B 21/0628 482/101 |
| 2015/0065302 A1 | * | 3/2015 | Ou | A61B 5/11 482/8 |

(Continued)

FOREIGN PATENT DOCUMENTS

CN 205626851 * 10/2016

*Primary Examiner* — Sundhara M Ganesan
*Assistant Examiner* — Shila Jalalzadeh Abyaneh
(74) *Attorney, Agent, or Firm* — Richard Eldredge; Eldredge Law Firm

(57) ABSTRACT

A device for logging exercise data, the device includes a body for engaging with an exercise machine; an electrical system with a power source incorporated into the body and to record data; an image sensor incorporated into the body and to capture an image; a motion sensor incorporated into the body and to detect movement; the image sensor determines a weight load associated with the exercise machine; the motion sensor detects and records a number of repetitions of movement; and the device creates an exercise log associated with a user's workout.

17 Claims, 11 Drawing Sheets

(56) References Cited

U.S. PATENT DOCUMENTS

| | | | | |
|---|---|---|---|---|
| 2016/0346617 A1* | 12/2016 | Srugo | ............... | G09B 19/0038 |
| 2017/0368413 A1* | 12/2017 | Shavit | ............... | G06K 9/00342 |
| 2018/0200561 A1* | 7/2018 | Chen | ................... | A63B 21/063 |

* cited by examiner

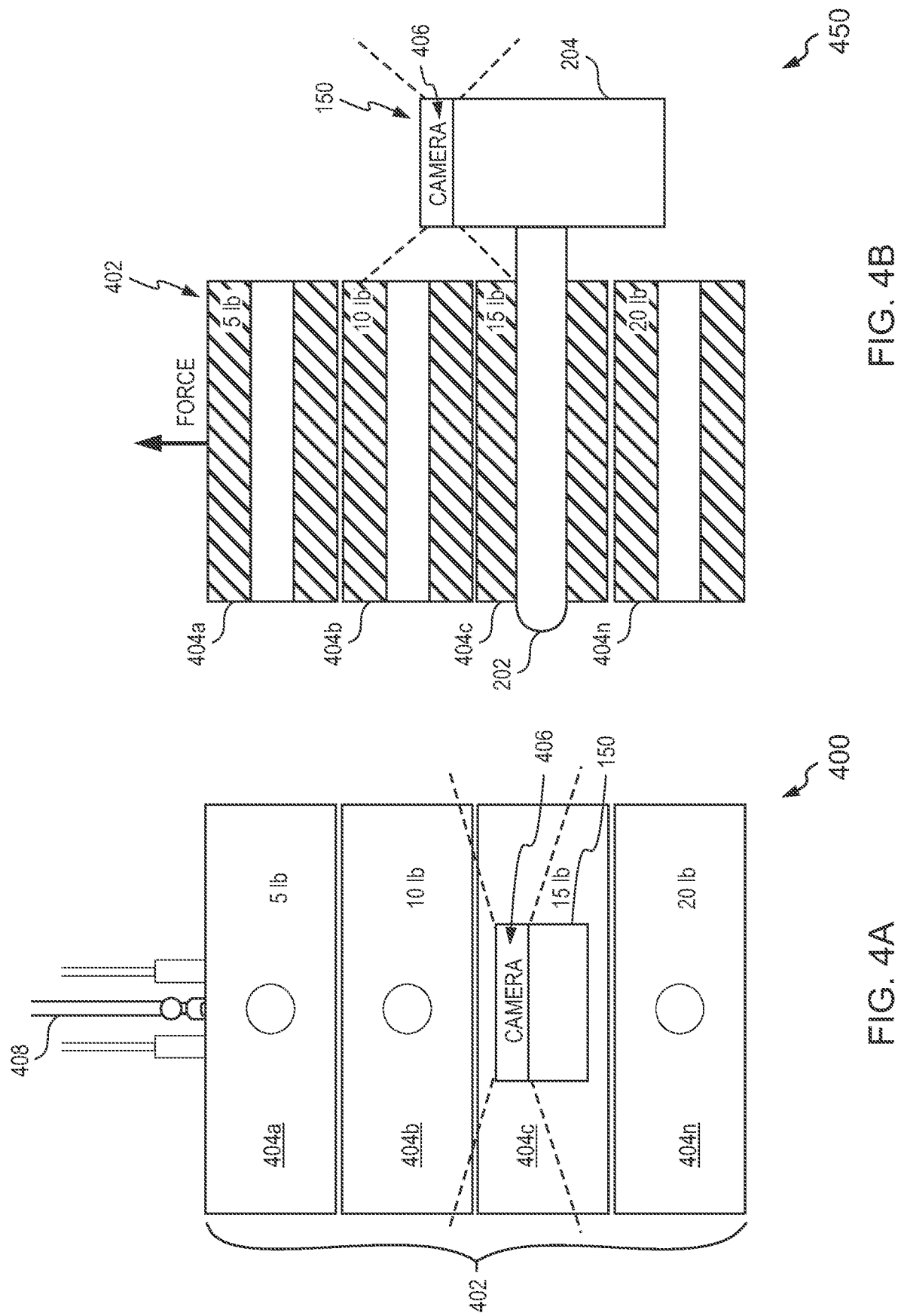

DEVICE FOR LOGGING EXERCISE DATA AND METHOD THEREOF

BACKGROUND

1. Field of the Invention

The present disclosure generally relates to data tracking aids associated with health and fitness activities and, more particularly to a device and a method for logging exercise data.

2. Description of Related Art

People involved in health and fitness related activities generally wish to track their personal performance and progress. For example, individuals involved in regular exercise sessions in a gymnasium (also referred to herein as 'gym') may wish to record a type of exercise, number of repetitions, number of weight-training sets with corresponding weight count, etc. for each exercise session to accomplish their respective fitness goals.

A shortcoming of conventional weight training machines and other types of exercise equipment (hereinafter collectively referred to as workout machines) is that they do not provide a convenient way for users to track and record their progress after their use of the workout machines. As a result, a user engaged in exercises (also referred to herein as workouts) often must rely on memory to keep track of how many weights were lifted during a workout, or how many repetitions were performed on a machine.

Alternatively, the user needs to carry a notebook and a pen to manually record information related to the workouts. Further, mobile applications for tracking user fitness also require the user to manually enter the relevant exercise data to keep track of the workouts. All such approaches are quite tedious for the user. Moreover, wearable fitness tracker devices can detect only a few types of exercise activities such as counting the number of repetitions per set (for example, number of steps taken, etc.) and therefore, provide only partial information to the user. Further, the conventional workout machines deployed in the gym are associated with several different manufacturers, and do not usually have power source and/or communication interfaces to send exercise data to the user's personal devices. Since most gym owners have already invested a huge amount for installing and maintaining the machines, they are unlikely to be replaced by smart workout machines until broken.

Accordingly, there is a need to overcome the drawbacks and enable the user to log exercise data in an improved and automated manner. More specifically, there is a need to enable the user to log exercise data without manually recording entries in the notebook or on the mobile application for any type of exercise.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 4A shows a representation of the device of FIG. 2A engaged in a weight stack of a weight stack machine for illustrating logging of exercise data, in accordance with an example embodiment of the invention;

FIG. 4B shows a side-view representation of the device of FIG. 2A engaged in the weight stack of FIG. 4A for illustrating logging of exercise data, in accordance with an example embodiment of the invention;

Figure 1:
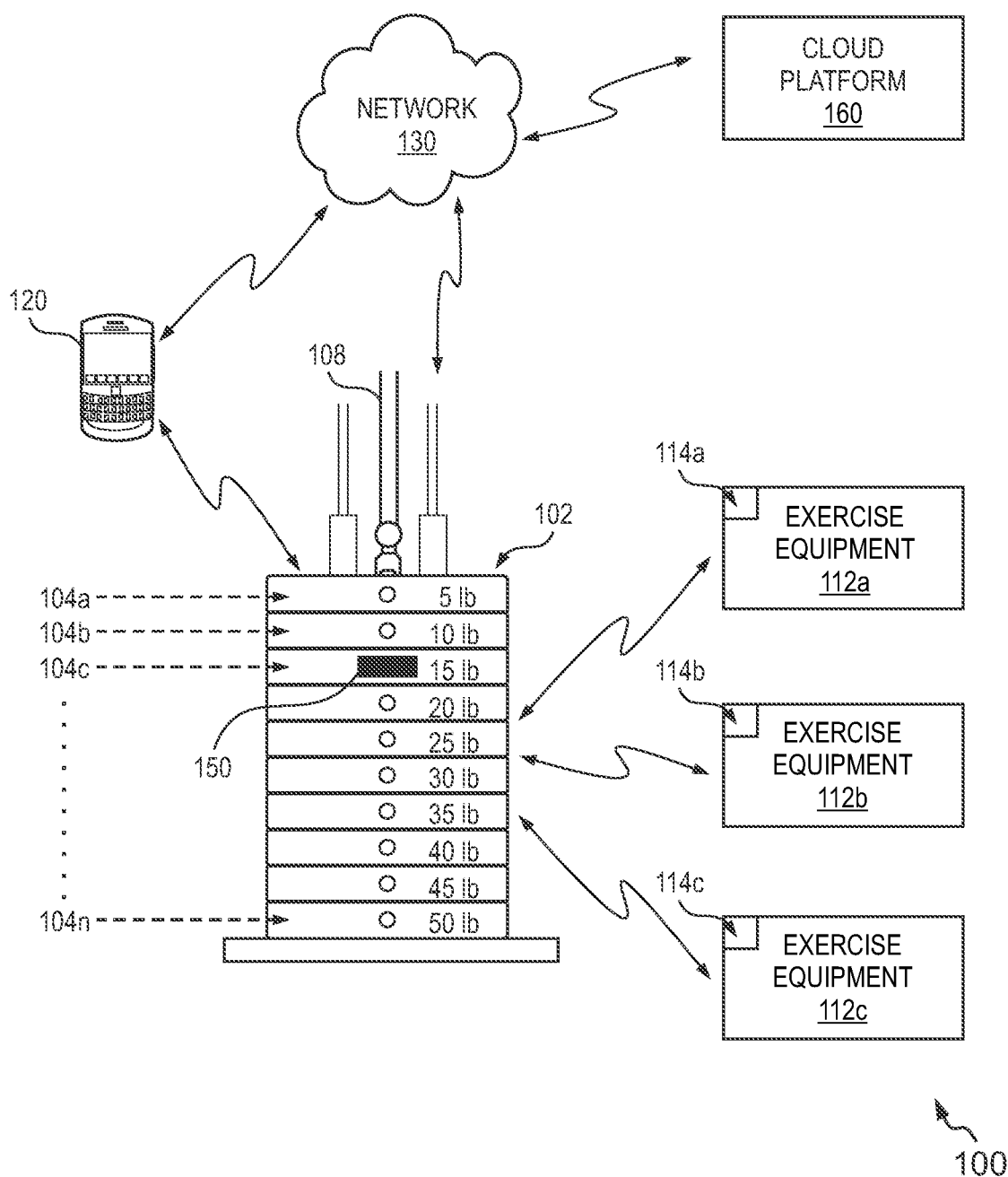
FIG. 1 shows a representation of an environment for logging exercise data, in accordance with an example embodiment of the invention.

The drawings referred to in this description are not to be understood as being drawn to scale except if specifically noted, and such drawings are only exemplary in nature.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The best and other modes for carrying out the present invention are presented in terms of the embodiments, herein depicted in FIGS. 1 to 10. The embodiments are described herein for illustrative purposes and are subject to many variations. It is understood that various omissions and substitutions of equivalents are contemplated as circumstances may suggest or render expedient, but are intended to cover the application or implementation without departing from the spirit or the scope of the present invention. Further, it is to be understood that the phraseology and terminology employed herein are for the description and should not be regarded as limiting. Any heading utilized within this description is for convenience only and has no legal or limiting effect. The terms "a" and "an" herein do not denote a limitation of quantity, but rather denote the presence of at least one of the referenced item.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Various embodiments disclosed herein provide a device and a method for logging exercise data. Conventional solutions for logging exercise data require the user to manually record entries by either using a pen and paper or using a fitness tracking application. Manually entering the type of exercises and keeping track of repetitions is tedious and inconvenient for the user. This may affect the overall workout regime of the user and, in turn, his/her fitness.

Stackable weight training machines generally include a mechanical weight stack pin use, in which the user may select the amount of weights he/she wants to lift during a weight training session. In one embodiment of the invention, a device capable of replacing the conventional weight stack pin used in the stackable weight training machines is disclosed. The device includes one or more sensors such as an image sensor (one or more cameras) and a motion sensor (accelerometer, gyroscope and/or magnetometer). The camera captures the image of the weight labels on weight plates of the weight stack machine and determines the weight via image processing techniques. The motion sensor allows a user to seamlessly capture the workout data, including the number of repetitions, sets and the way the exercise was performed. Further, the device includes a detachable portion, which may be used to log exercise data related to other forms of weight training and non-weight training exercises, such as running and bicycling for instance.

In one embodiment of the present invention also provides robust user identification while ensuring correct data is logged. Further, a combination of Bluetooth beacons and motion sensing of the device enables identification of the type of workout machine. This further helps in accurate determination of the type of exercise the user was engaged in. Thus, the device of the present invention captures a much more detailed log of user's workout with all the above features combined. The device is also configured to communicate with the user's personal electronic devices (e.g. smart watch, smartphone, PC, fitness tracker device) directly and/or send the data to a cloud platform for storage, thereby ensuring easy access and prevention against data loss.

FIG. 1 shows a representation of an environment 100 for logging exercise data, in accordance with an example embodiment of the invention. In one embodiment, the environment 100 may correspond to a gymnasium (also referred to herein as 'gym'). The environment 100 is depicted to include a weight stack 102. The weight stack 102 may be a part of a stackable weight-training machine (not shown). The stackable weight-training machine may be configured to enable a user to perform exercise routines, such as bar throw and press, calf press, hamstrings curls, chest press and the like. More specifically, the stackable weight-training machine may provide specific muscle oriented workouts or alternatively may combine one or more different muscle groups in one machine.

The weight stack 102 includes a plurality of rectangle weight plates 104a, 104b, 104c to 104n (hereinafter referred to as weight plates 104a-n). Each weight plate has corresponding weight assigned to enable a user to select desired weight for a workout session (for example 5 lbs., 10 lbs., 15 lbs., etc.). A vertical lifting bar 108 is shown passing through the weight plates 104a-n. The vertical lifting bar 108 is hereinafter referred to as lift bar 108. The lift bar 108 includes a plurality of holes, which can align with holes in the weight plates 104a-n, to enable selection of the weight plates for performing an exercise routine. A user may insert a pin through a hole when aligned with a hole in the lift bar 108 to provide the selection of the weight for an exercise routine. In the representation 100, the user is depicted to have selected 15 lbs. for the exercise routine. As the user goes through the exercise motion, the lift bar 108 rises and the pin supports all the weight plates stacked above it. The user may select different levels of resistance over the same range of motion by simply removing the pin from current weight plate (for example, weight plate 104c) and inserting the pin into the lift bar 108 at a desired weight level using the corresponding weight plate.

In at least one example embodiment, a device 150 is provided, which is embodied as a pin (or a smart pin) for use in stackable weight-training machines. The device 150 includes a shaft portion and a head portion (not shown in FIG. 1). The shaft portion of the device 150 can perform the same weight selection function as a regular pin used in stackable weight-training machines. The device 150 may be removably attached to the weight stack 102 as shown in the representation 100. The device 150 is configured to log data related to the user's workout sessions, as will be explained in greater detail with reference to FIGS. 2A to 10.

The environment 100 is further depicted to include several other types of exercise equipments (exemplarily depicted as blocks 112a, 112b and 112c). The exercise equipments 112a-112c may correspond to weight training machines, non-weight training machines (such as treadmills, cycles, etc.), and the like. The various types of exercise equipments are hereinafter collectively referred to as workout machines. Each workout machine may be associated with a respective universally unique identifier (UUID). The UUID may enable identification of the respective workout machine.

In the representation 100, each workout machine is depicted to be associated with a signaling device. For example, the exercise equipments 112a, 112b and 112c are depicted to be associated with signaling devices 114a, 114b and 114c, respectively. In one embodiment, the signaling device may be embodied as a Bluetooth module capable of transmitting beacons. For example, the Bluetooth modules may use Bluetooth low energy proximity sensing to transmit the UUID to nearby electronic devices, such as the device 150 and/or to personal computing devices of the users. The device 150 may be configured to receive the beacons transmitted by the workout machines and use the beacons to identify the type of exercise equipment as well as the type of exercise.

The environment 100 is further exemplarily depicted to include one user device 120. The user device 120 is exemplarily depicted to be a smartphone. It is understood that the environment 100 may include several electronic devices associated with a plurality of users using the workout machines in the environment 100. Some other non-exhaustive examples of the user device 120 may include a wearable device, a cellular phone, a tablet computer, a laptop, a personal digital assistant (PDA), a fitness tracker device such as a smart watch, and the like.

The user device 120 may be configured to receive exercise data logged from the device 150. The user device 120 may further be configured to provide feedback to the user in real time in the form of live workout tips videos, textual messages, web-based UIs, vibrations, etc. The communication between the user device 120 and the device 150 may be facilitated over a network 130. An example of the network 130 may include a Wi-Fi network (implemented, for example, by using a wireless local area network (WLAN)). It is noted that the device 150 may communicate with personal devices of several users. Furthermore, such communication may be achieved using other forms of networks, including wired networks, wireless networks and combinations thereof. For example, the device 150 may connect to the Internet using a cellular network to establish communication with a personal device of the user. Accordingly, the network 130 may include any such form of wired and/or wireless network capable of facilitating communication between the device 150 and remote entities, such as the personal devices of the users. The environment 100 further depicts a cloud platform 160. The cloud platform 160 may include a database and a cloud-based application for facilitating storage and retrieval of exercise data. The device 150 may be configured to in operative communication with the cloud platform 160 using the network 130. In some embodiments, the exercise data related to one or more users may be logged in the database associated with the cloud platform 160. The device 150 facilitating logging of exercise data is explained hereinafter with reference to FIGS. 2A to 8.

Figure 2A:
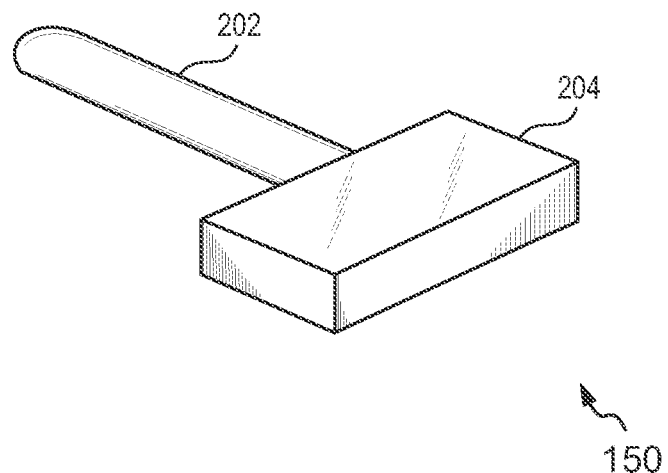
FIG. 2A shows a perspective view of a device configured to facilitate logging of exercise data, in accordance with an example embodiment of the invention.

FIG. 2A shows a perspective view of the device 150 configured to facilitate logging of exercise data, in accordance with an example embodiment of the invention. As shown, the device 150 includes a shaft portion 202 and a head portion 204. The shaft portion 202 extends outwardly from the head portion 204.

As explained with reference to FIG. 1, the shaft portion 202 is capable of being inserted in a hole/channel associated with a weight plate and thereafter engage with a hole in a lift bar associated with a stackable weight-training machine to enable selection of weight for performing a weight-training exercise routine. In various embodiments, the shaft portion 202 may be composed of metal, metallic alloys, composite materials, or the like.

The head portion 204 is detachably coupled to the shaft 202. In an embodiment, the head portion 204 may be magnetically attached to the shaft 202. In some embodiments, the device 150 may can accommodate different types of shaft, which can fit into several weight stack machines of different configurations and can work with older machines as well.

The head portion 204 is depicted to have a rectangular shaped-body for illustration purposes. It is noted that the head portion 204 may be configured in any other shape, such as a square-shape, spherical shape, etc. to facilitate ease of handling the device 150. The head portion 204 is configured to include one or more electronic components (or modules), which together are configured to facilitate logging of exercise data as will be explained in detail with reference to FIGS. 3A, 3B, 4A and 4B.

As the head portion 204 is detachably attached to the shaft portion 202, in some embodiments, the head portion 204 may be asymmetrically coupled to the shaft portion 202. Such a configuration is depicted in FIG. 2B.

Figure 2B:
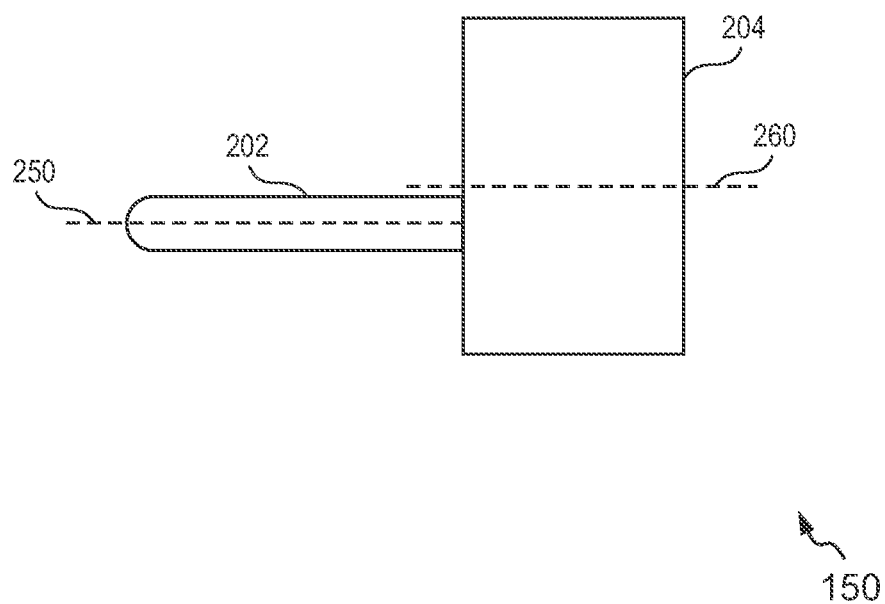
FIG. 2B shows a representation for illustrating asymmetric coupling between a shaft portion and a head portion of the device of FIG. 2A, in accordance with an example embodiment of the invention.

FIG. 2B shows a representation for illustrating asymmetric coupling between the shaft portion 202 and the head portion 204 of the device 150, in accordance with an example embodiment of the invention. As shown, the head portion 204 is asymmetrically attached, i.e. a central axis of the shaft portion 202 (shown using a dotted line 250) is not aligned with a central axis of the head portion 204 (shown using a dotted line 260). In some embodiments, the head portion 204 may be configured to self-align such that the central axes overlap as soon as the user inserts the shaft portion 202 of the device 150 into the weight plates of the stackable weight-training machine. The asymmetric alignment causes center of gravity of the head portion 204 to be lower and therefore every time the device 150 is inserted into the weight plates, the head portion 204 aligns itself. The asymmetric alignment of the head portion 204 may assist in capturing a range of weight labels of weight stack, as will be explained later with reference to FIGS. 4A and 4B.

Figure 3A:
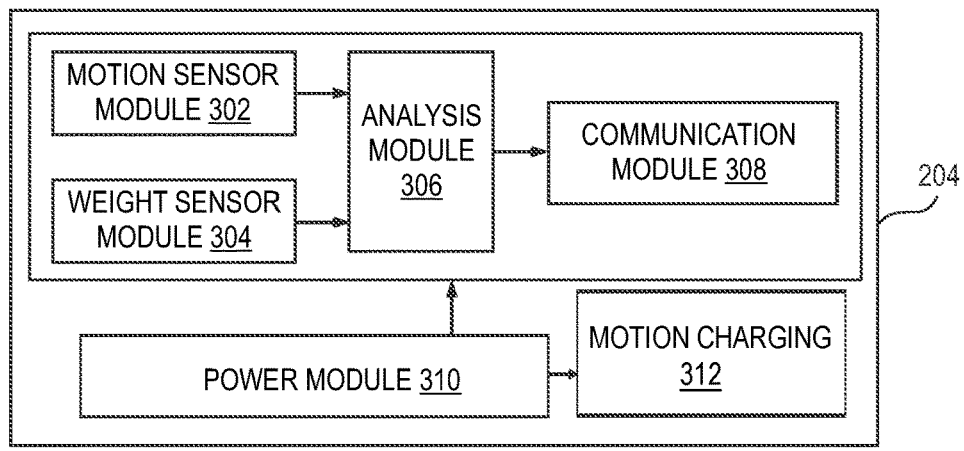
FIG. 3A illustrates a block diagram representation of the head portion of the device of FIG. 2A, in accordance with an example embodiment of the invention.

FIG. 3A illustrates a block diagram representation of the head portion 204 of the device 150, in accordance with an example embodiment of the invention. The head portion 204 is depicted to include a motion sensor module 302, a weight sensor module 304, an analysis module 306, a communication module 308 and a power module 310. In some embodiments, the head portion 204 can further include a motion based charging module 312 configured to utilize the motion of the exercise equipment to generate current which is either then stored energy or used by the system.

The various components of the head portion 204, such as the motion sensor module 302, the weight sensor module 304, the analysis module 306, the communication module 308 and the power module 310 may be configured to communicate with each other via or through a centralized circuit system. The centralized circuit system may be various devices configured to, among other things, provide or enable communication between the components (302-310) of the head portion 204. In certain embodiments, the centralized circuit system may be a central printed circuit board (PCB) such as a motherboard, a main board, a system board, or a logic board. The centralized circuit system 210 may also, or alternatively, include other printed circuit assemblies (PCAs) or communication channel media.

The motion sensor module 302 may be configured to detect presence of motion and thereafter trigger weight sensing operation for facilitating logging of exercise data. To that effect, the motion sensor module 302 may include one or more sensors such as but not limited to an accelerometer, a gyroscope, a magnetometer, a vibration sensor and the like. The motion sensor module 302, in addition to detecting motion, may also be configured to sense motion parameters associated with a user's workout. For example, the motion sensor module 302 may detect direction of movement of the weights being lifted by the user, thereby facilitating counting of sets, repetitions, etc.

In one embodiment, the user may be asked to identify/name the machine during the first use of the device 150 on a given exercise/weight training machine. Thereafter, the user's acceleration profile i.e. changes in acceleration during the exercise as detected by the motion sensor module 302 may be used to predict the machine type as well as the exercise type.

In one example embodiment, the motion sensing information may be received using other sources such as the fitness tracker device of the user or one or more sensors present in a mobile phone of the user. The data received from the other sources may be used to supplement the data captured by the motion sensor module 302 to analyze the user's motion parameters more accurately. In one embodiment, the motion sensor module 302 may also be used for correcting weight data collected by the weight sensor module 304.

In an embodiment, the weight sensor module 304 may include one or more visual sensors (or cameras) to detect the load (weight) used for training by the user. The camera may capture visual information related to the weights in form of an image or a video, which may thereafter be processed to automatically identify the weight without user intervention. In one embodiment, the energy used by the camera may be optimized, e.g. the camera may be only used when exercise motion is detected (and not based on any random motion of the user). Moreover, the energy optimization may be achieved by using the camera only once during an exercise set since the weight during an exercise set (for example, a set of 12-15 repetitions) remains the same. In some embodiments, the camera may be continuously used during the full set to count number of repetitions performed by the user, thereby precluding the need to involve the motion sensor module 302. The device 150 may, in turn, provide the number repetitions in real time to the user through a display (or provide visual clues like light turning on or off or with light color changes) or voice notifications so that the user does not have to remember the count of repetitions while working out. In an example embodiment, a plurality of cameras may be mounted on the device 150 to get information regarding the type of exercise and type of machine. For example, the camera may be used to capture images of the weight-training machine, while the user is exercising and the images may be analyzed by the analysis module 306 to identify the machine. Alternatively, the user may be prompted to select the machine from many machine types provisioned to him/her for the first time he/she uses the device 150. Thereafter, the device 150 may use the captured images of the machine or retrieve the user selections to identify the machine for subsequent usage.

In one embodiment, the camera may be used to capture one or more images of each user of the device 150. The images of each user may be stored with corresponding facial features (for example, features identified using face detection algorithms). In at least one example embodiment, each user may be assigned a unique identification number (UID) to facilitate user identification. The subsequent use of the device 150 by a user may cause the camera to identify the user using the captured image and recorded facial features. The user's exercise data may thereafter be correctly logged for each respective user.

In an embodiment, the analysis module 306 may be configured to perform one or more logical operations on the data received from other modules of the device 150. To that effect, the analysis module 306 may include a microprocessor or a microcontroller to perform the logical operations. In some embodiments, the analysis module 306 may also include, among other components, a memory such as a flash memory. The memory may be configured to store machine executable instructions for the microcontroller to perform one or more analytical operations. In some embodiments, the memory may also include algorithms, such as face detection algorithms (for example, for identifying users etc.) or image processing algorithms (for example, for identifying weight labels, machines, and the like).

Amongst various other tasks, the analysis module 306 may be configured to process data received from the weight sensor module 304 to estimate the weight lifted by the user 102. The analysis module 306 may utilize one or more algorithms such as image processing algorithms and machine learning algorithms to estimate the weight. Further, the analysis module 306 may process raw weight and/or motion data to provide a more accurate estimate of weight and/or motion. The analysis module 306 may also predict the type of exercise based on the raw or processed weight and/or motion data and/or other available inputs. In some embodiments, the analysis module 306 may be configured to estimate one or more other workout parameters such as calories burned, time spent per workout session and the like, using the weight and/or motion data.

Further, the analysis module 306 may calculate power consumption of one or more other modules included in the head portion 204 of the device 150. Moreover, the analysis module 306 may be configured to predict the user's workout behavior and provide valuable feedback on the workout in real-time. In one embodiment, the analysis module 306 may also include its own power source or the analysis module 306 may share the power provided by the power module 310 with other modules of the device 150.

Thus, as explained above, the motion sensor module 302, the weight sensor module 304 and the analysis module 306 may be configured to capture information related to user workout sessions, such as the type of exercise, number of repetitions, weights involved, and the like. Moreover, in some embodiments, the information captured may also include data such as calories burned, time spent on a workout, etc. Such data may be logged as exercise data in the memory associated with the analysis module 306 and/or transmitted to the user device or cloud platform for storage purposes.

In an embodiment, the communication module 308 is configured to enable transmission of the data logged by one or more modules of the device 150. The communication module 308 may be configured to transmit the exercise data to the user device, such as the user device 120 shown in FIG. 1, and/or to a remote server embodying a cloud platform, for storing the data. To that effect, the communication interface 308 may include communication circuitry such as for example, a transceiver circuitry including antenna and other communication media interfaces to connect to a wired and/or wireless communication network. The communication circuitry may, in at least some example embodiments, enable transmission of data signals and/or reception of signals to and/or from network entities, such as the signaling devices associated with workout machines, personal computing devices of users, cloud platform, and the like. In an embodiment, the communication module 308 may be configured to communicate the exercise log data to other external storage devices using data ports like USB.

In an example embodiment, the communication module 308 may include mechanisms configured to receive inputs from and provide outputs to the user of the device 150. To that effect, the communication module 308 may include at least one input interface (not shown) and/or at least one output interface (not shown). The one or more input and output interfaces are collectively referred to hereinafter as input/output (I/O) interface. Examples of the input interface may include, but are not limited to a keypad or a numeric pad, a touch screen or a dial screen, soft keys, a microphone, and the like. Examples of the output interface may include, but are not limited to, a UI (User Interface) display (such as a light emitting diode display, a thin-film transistor (TFT) display, a liquid crystal display, an active-matrix organic light-emitting diode (AMOLED) display, etc.), a microphone, a speaker, a ringer, a vibrator, and the like.

In some embodiments, the user may provide manual data input using the I/O interface of the communication module 308. For example, the user may manually enter weight of dumbbells being lifted using the numeric pad of the I/O interface. The communication module 308 may store the input from the user in the memory of the analysis module 306 or pass such information to other modules of the device 150.

In an embodiment, the power module 310 may be responsible for providing power to other modules of the device 150. The power module 310 may use one or more batteries (such as one or more lithium-ion batteries, button-type batteries, a dry cell battery, etc.) and/or external power sources. The power module 310 may also include a power generating mechanism (e.g. a generator, induction based electricity generator etc.), which uses the workout energy to generate power for the device 150. The power module 310 may also include a unit capable of harnessing power wirelessly. In an embodiment, the device 150 may be configured to automatically go to a "standby" mode when it detects a lack of movement and/or load for a predetermined period to reduce the power consumption.

In an embodiment, the device 150 may include more or fewer components than those explained with reference to FIG. 3A. For example, in one embodiment, the device 150 may perform only weight and motion detection tasks and the rest of the computation on motion and weight data may be done remotely outside the device 150. More specifically, the head portion 204 of the device 150 may preclude the analysis module 306 and only include the motion sensor module 302, the weight sensor module 304, the communication module 308 and the power module 310. Alternatively, all the computation may happen on the head portion 204 including inferring of the exercise type based on motion and/or weight data and/or correction of weight data, as explained above. In an embodiment, the head portion 204 may not include the weight sensor module 304. The head portion 204, in such a scenario, may be used to measure motion for exercises where the weight data is hard to gather automatically. For example, when the user is using dumbbells for working out. In such a case, the weight data can be entered manually by the user using the I/O interface of the communication module 308 of the head portion 204. In one embodiment, the head portion 204 can be partly detached from the shaft portion 202 of the device 150. For example, only the motion sensor module 302 (or the accelerometer within the motion sensor module 302) and the communication module 308 (or a Bluetooth component of the communication module 308) along with the power module 310 can be detached from the shaft portion 202. In another embodiment, the head portion 204 or only a detached part of the head portion 204 can be placed on top of the weight stacks to monitor/capture the motion data. Further, the head portion 204 can be placed on top of the weight stacks such that the camera is facing down towards the weight labels to capture the weight data. In one embodiment, the sensing of motion and motion related parameters and the subsequent analysis of the weight and motion data may be performed on the user device and the head portion 204 may preclude the motion sensor module 302 and the analysis module 306. Such a scenario is depicted in FIG. 3B.

Figure 3B:
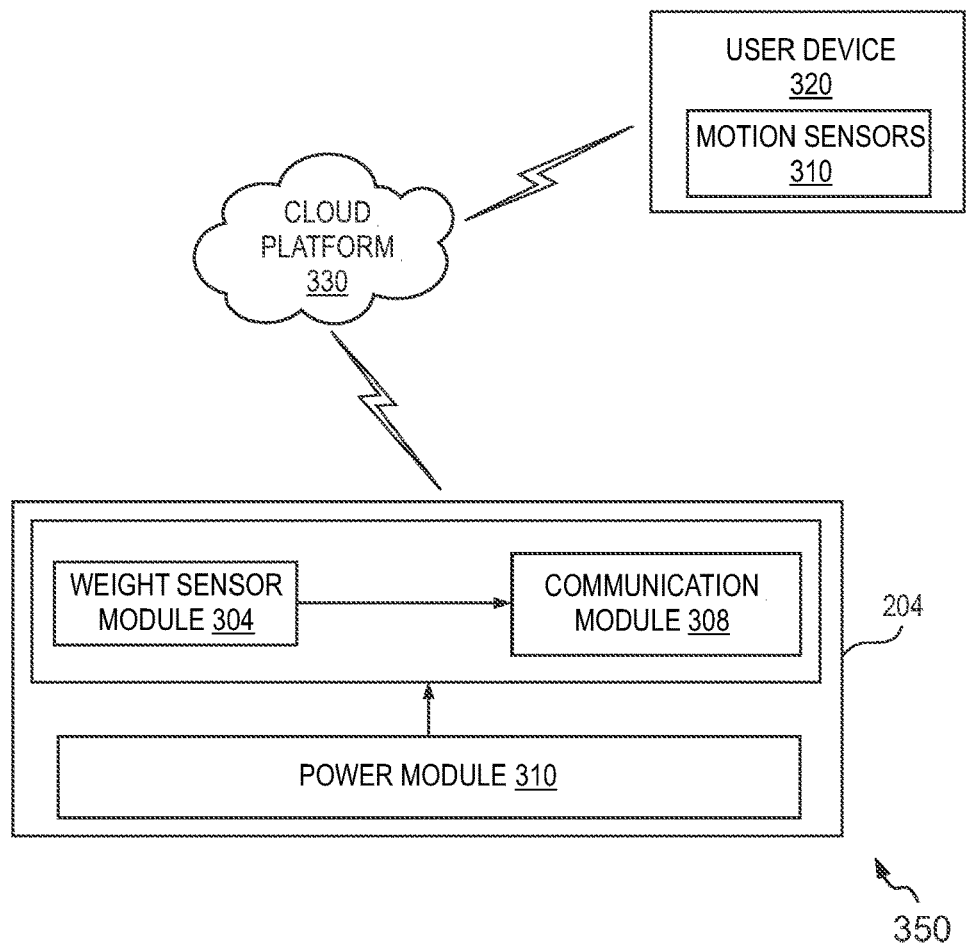
FIG. 3B illustrates a block diagram representation of the head portion of the device of FIG. 2A, in accordance with another example embodiment of the invention.

FIG. 3B illustrates a block diagram representation 350 of the head portion 204 of the device 150, in accordance with another example embodiment of the invention. As shown in the representation 350, the head portion 204 may be configured to include only the weight sensor module 304, the communication module 308 and the power module 310. In such scenarios, the data related to motion of the user's exercise may be collected from motion sensors 311 included in a user device 320 (such as a fitness tracker device or a mobile phone). Further, the head portion 204 of the device 150 may transmit captured weight data to the user device 320 or to the cloud platform 330 so that the data can be processed remotely and retrieved later as and when requested by the user. For example, the device 150 may be configured to directly connect with a cloud application stored in the cloud platform 330. Alternatively, the device 150 may access the cloud platform 330 using the user device 320. The cloud application in the cloud platform 330 may be configured to process the weight data received from the device 150 along with the motion data received from the motion sensors 311 in the user device 320 and log the processed data as exercise data in a database associated with the cloud platform 330. The cloud platform 330 may allow easy access to the logged exercise data and prevent against data loss. In one embodiment, the communication module 308 may can facilitate operative communication with the cloud application in the cloud platform 330 or a data logging application in the user device 320 using API calls over a communication network, such as the network 130 explained with reference to FIG. 1. The data logging application in the user device may also contain predictive algorithms, which use the data to predict workout parameters such as exercise type based on motion profiles. It may also be used to predict user behavior and accordingly provide user feedback to help the users reach their goals and/or help them perform their workout correctly by way of for example, guided live or recorded workout session videos. One such user device is explained later in detail with reference to FIG. 10.

FIG. 4A shows a representation 400 of the device 150 engaged in the weight stack 402 of the weight stack machine (not shown) for illustrating logging of exercise data, in accordance with an example embodiment of the invention. The weight stack 402 includes a plurality of rectangle weight plates 404a, 404b, 404c and 404n (hereinafter referred to as weight plates 404a-n). Each weight plate has corresponding weight assigned to enable a user to select desired weight for a workout session (for example 5 lbs., 10 lbs., 20 lbs. etc.). It is understood that each weight plate weighs 5 lbs. and the corresponding number written on the successive weight plates represents the total weight that the user would lift if a corresponding weight plate is selected as the final weight plate above the pin (i.e. above the device 150). A lift bar 408 is shown passing through the weight plates 404*a-n*. The lift bar 408 includes a plurality of holes, which can align with holes in the weight plates to enable selection of the weight plates for performing an exercise routine.

A user is depicted to have inserted the device 150 through a hole in the weight plate 404*c* (marked with 15 lbs.). The hole in the weight plate 404*c* is aligned with a hole in the lift bar 408 to provide the selection of the weight (i.e. 15 lbs) for an exercise routine. As the user goes through the exercise motion, the lift bar 408 rises and the device 150 supports all the weight plates stacked above it as shown by the upward direction of force in FIG. 4B. As explained with reference to FIG. 3A, the weight sensor module 304 of the device 150 includes a visual sensor (shown as a camera 406 in the representation 400). A viewing range of the camera 406 for capturing image/video of surrounding environment is exemplarily shown as a region bounded by dotted lines in respective directions. The viewing range may be enhanced by use of optical lens e.g. wide angle or fish eye lens. In an embodiment, the camera 406 is used to capture visual information related to the weights that the user is currently lifting. More specifically, the camera may capture the weight labels (for example, 15 lbs.) that the user is currently lifting. This visual information can be captured in form of an image or a video, which may be processed on the device 150 and/or on the user device (or in some embodiments, on the cloud platform) to obtain the weight that the user has selected.

FIG. 4B shows a side-view representation 450 of the device 150 engaged in the weight stack 402 of FIG. 4A for illustrating logging of exercise data, in accordance with an example embodiment of the invention. As can be seen, the camera 406 is integrated in the head portion 204 of the device 150. The shaft portion 202 is shown inserted into corresponding hole of the weight plate 404*c* by the user.

As explained with reference to FIGS. 2A and 2B, the head portion 204 is capable of being detached from the shaft portion 202 and moreover, can be asymmetrically attached to the head portion 204. In some embodiments, the head portion 204 may move automatically to maintain the camera orientation between different exercises and it may further enable the camera 406 to capture various views of the surrounding environment which may include such as but not limited to, the user, the weight labels printed on the weight plates 404*a-n*, the weight training machine, the weight numbers written on other exercise equipments such as dumbbells or kettle bells and the like. In scenarios, where weight label is absent, the camera 406 may be configured to deduce the label based on the surrounding weight labels. The weights lifted and the number of repetitions may be recorded using the combination of the motion sensor module 302, the weight sensor module 304 and the analysis module 306 as explained with reference to FIG. 3A. Such data may then be logged as 'exercise data' in the memory of the analysis module 306 and/or provisioned to a fitness application (also referred to herein as data logging application) in the user device. It is noted that the exercise data may include data related to non-weight training related exercises too, as will be explained next with reference to FIGS. 5 and 6.

Figure 5:
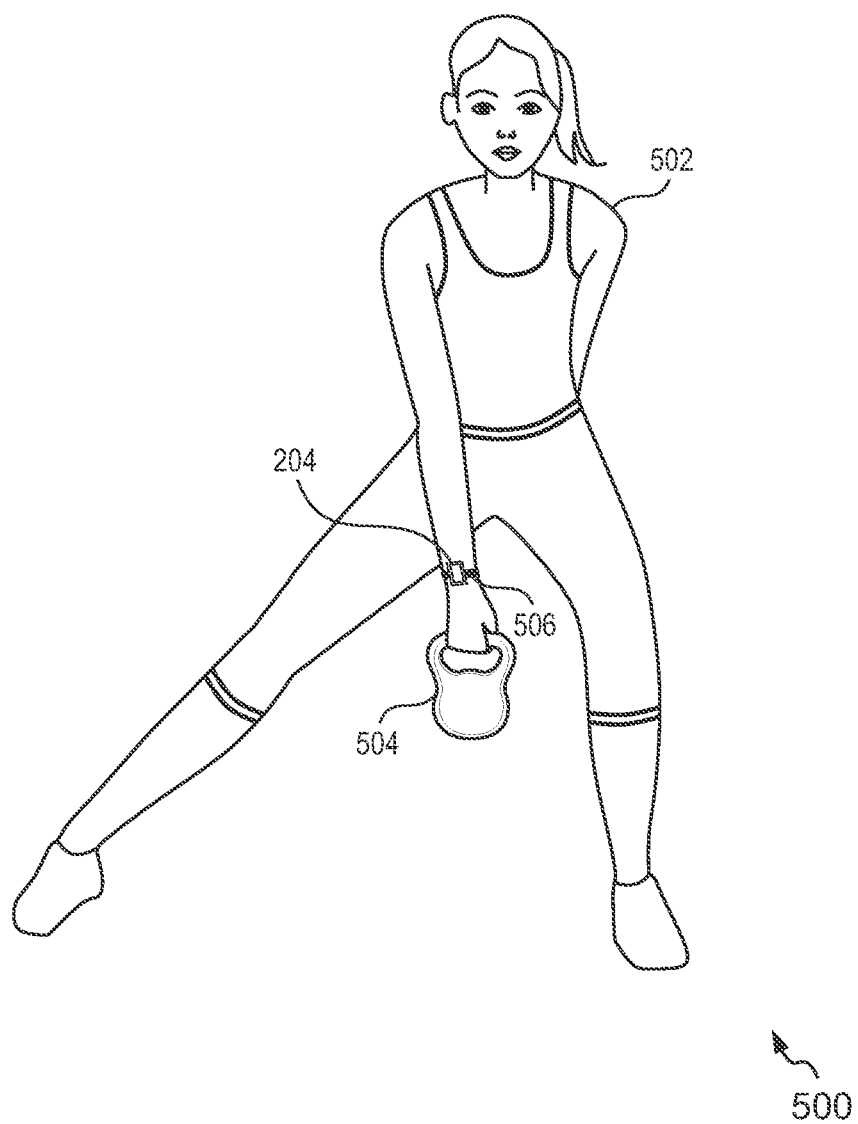
FIG. 5 shows a representation of the head portion of the device of FIG. 2A worn by a user for logging of exercise data, in accordance with an example embodiment of the invention.

FIG. 5 shows a representation 500 of the head portion 204 of the device 150 worn by a user for logging of exercise data, in accordance with an example embodiment of the invention. As explained with reference to FIG. 3A, the head portion 204 may be detached from the shaft portion 202. The use of the detached head portion 204 for logging of exercise data is explained hereinafter.

The representation 500 depicts a user 502 lifting a kettle bell 504. Further, the head portion 204 of the device 150 is shown worn by the user 502 using a wristband 506 (or a bracelet) on the wrist of the user 502. In some embodiments, the head portion 204 may also include a clip or other attachment feature (e.g., Velcro, a flexible band or strap, etc.) for releasably securing the head portion 204 to a belt, or other article of clothing worn by the user 502. In other embodiments, the user 502 may carry the head portion 204 in other ways such as in the cloth pocket to record the number of repetitions of callisthenic-type exercises (e.g., chin-ups, sit-ups, leg lifts, etc.) or free-weight exercises (e.g., curling, bench-press, and other barbell exercises).

The camera included in the weight sensor module 304 of the head portion 204 may capture images of the kettle bell 504 to read the weight label attached to the kettle bell 504 to estimate the amount of weight the user 502 is lifting. Further, the motion sensor module 302 in the head portion 204 may enable to detect number of repetitions completed by the user 502 using the kettle bell 504. In some embodiments, the range of motion sensed by the motion sensor module 302 may facilitate in determining the type of exercise automatically. The head portion 204 may communicate the logged exercise data to a mobile phone of the user 502 using the communication module 308 and the user 502 may view real time exercise data logs on the mobile application running on her mobile phone.

In one embodiment, the camera may also be used to capture images of the user 502 and the analysis module 306 may identify the user 502 by processing those images. In some embodiments, the user identification may be achieved for example, by pairing the user device with the device 150, using a user specific login information (e.g. password, fingerprints, or other biometric identification methods) on the weight training machine/the device 150/the paired user device. In some embodiments, using one or more voice/ face/biometric information recognition methods installed on the device 150/the user device/the weight training machine may ensure that the data collected by the device 150 is attributed only to the rightful owner of the device and the like. In an example embodiment, barcodes or RFID (Radio Frequency identification) tags, QR (Quick Response) codes may also be used to identify the user.

Figure 6:
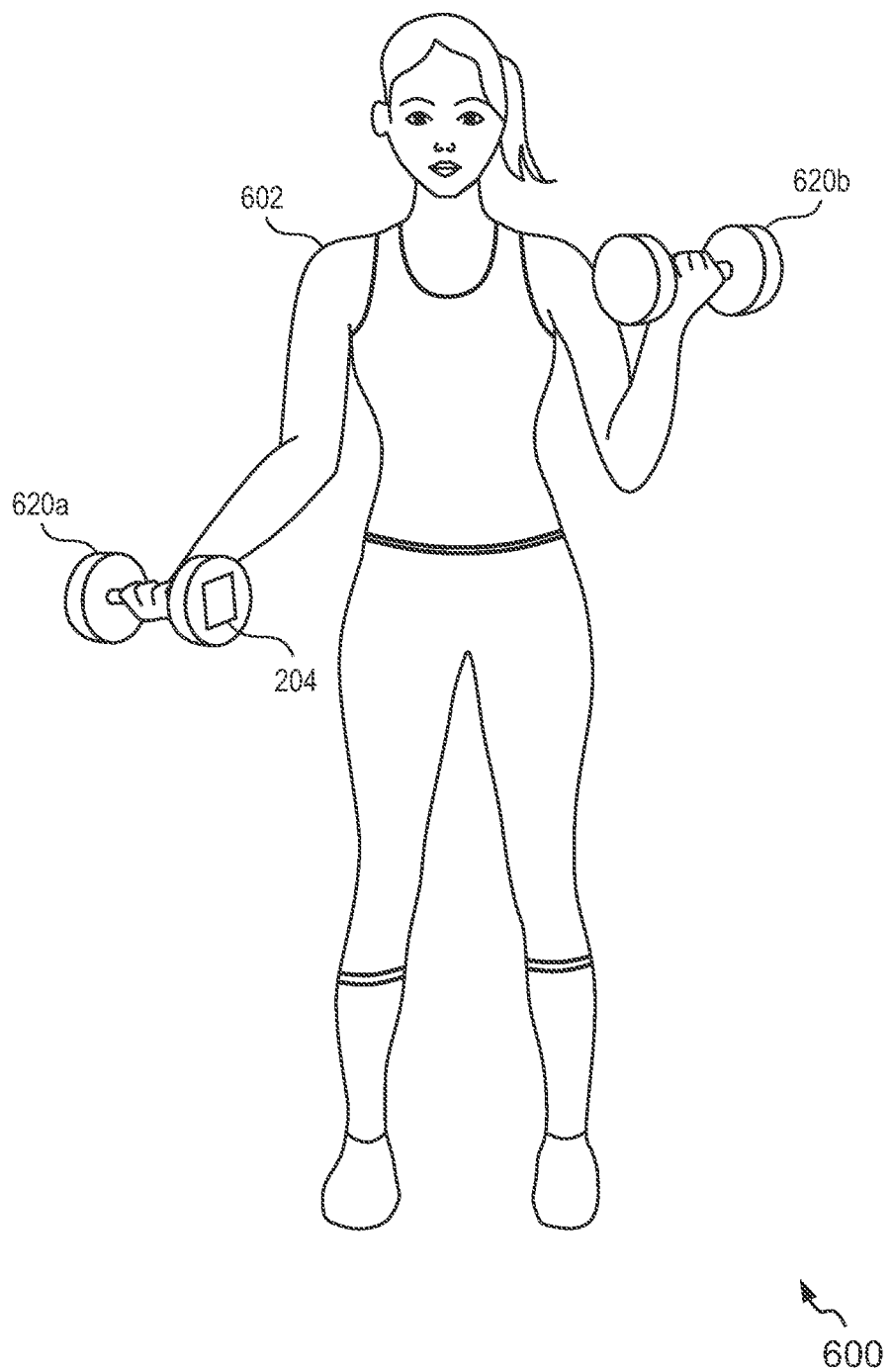
FIG. 6 shows a representation of the head portion of the device of FIG. 2A attached to exercise equipment for logging of exercise data, in accordance with an example embodiment of the invention.

FIG. 6 shows a representation 600 of the head portion 204 of the device 150 attached to exercise equipment for logging of exercise data, in accordance with an example embodiment of the invention. As explained with reference to FIG. 3A, the head portion 204 may be detached from the shaft portion 202. The detached head portion 204 may then be attached to a dumbbell, such as the dumbbell 620*a* by way of any type of detachable connection as shown in the representation 600. In some embodiments, the head portion 204 may include a magnet or a suction cup (not shown) on one side such that it is capable of being attached to exercise equipments such as dumbbells, kettle bells, barbells and the like.

The camera included in the weight sensor module 304 of the head portion 204 may capture images to read the weight label attached to the dumbbell 620*a* or 620*b* to know the amount of weight the user 602 is lifting. Further, the motion sensor module 302 of the head portion 204 may enable detection of number of repetitions completed by the user 602 using the dumbbells 620*a-b*. In some embodiments, the range of motion sensed by the motion sensor module 302 may facilitate in determining the type of exercise automatically. The head portion 204 may communicate the logged exercise data to a mobile phone of the user 602 using the communication module 308 and the user 602 may view real time exercise data logs on the mobile application running on her mobile phone.

Figure 7:
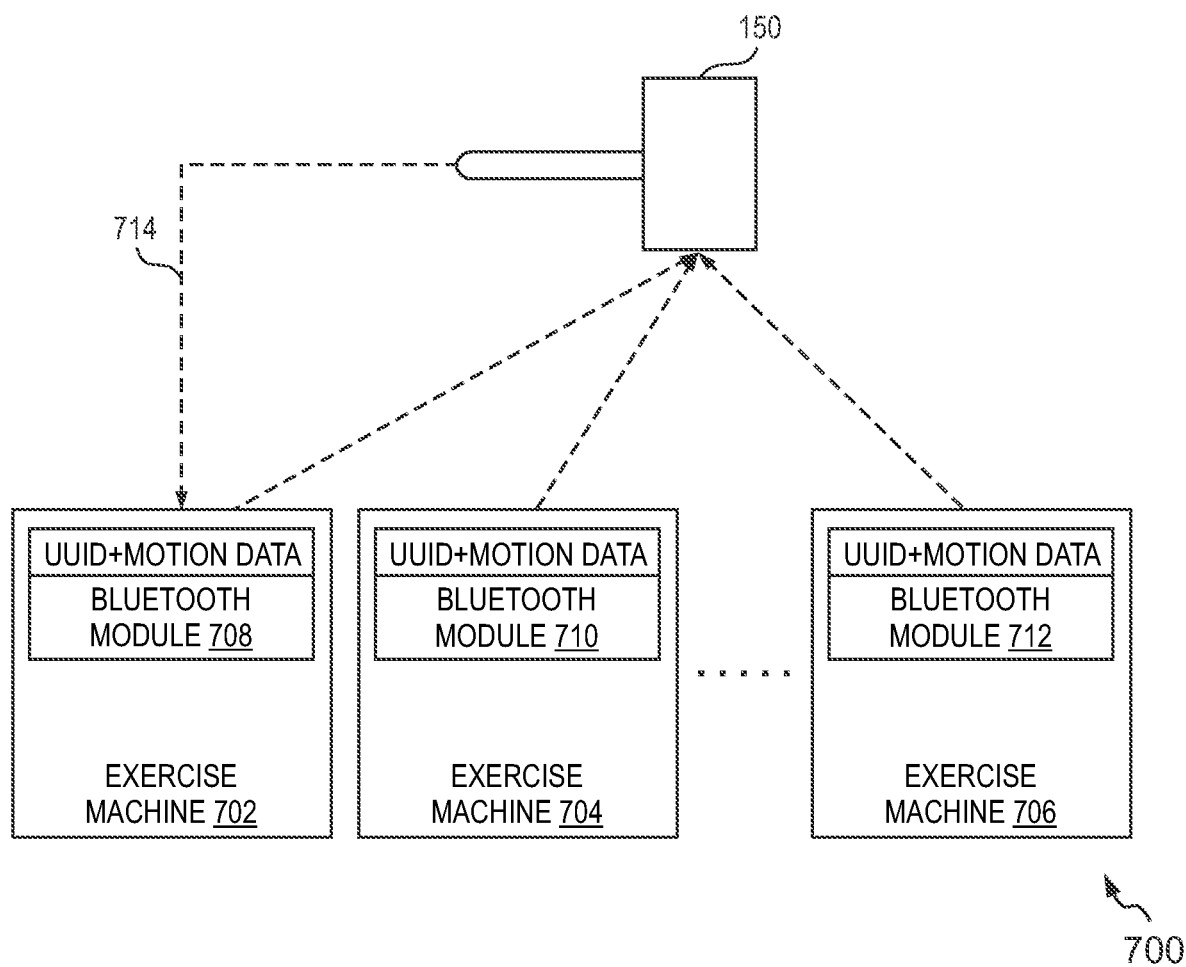
FIG. 7 illustrates a block diagram representation for illustrating communication between the device and various exercise machines, in accordance with an example embodiment of the invention.

FIG. 7 illustrates a block diagram representation 700 for illustrating communication between the device 150 and various exercise machines, in accordance with an example embodiment of the invention. As explained with reference to FIG. 1, the various exercise (or workout) machines may include signaling devices, such as Bluetooth low-energy modules, capable of signaling, for example via beacons, to the device 150. Accordingly, the representation 700 exemplarily depicts three exercise machines 702, 704 and 706. Each exercise machine includes a Bluetooth module. For example, the exercise machines 702, 704 and 706 are depicted to include Bluetooth modules 708, 710 and 712, respectively. The Bluetooth modules 708, 710 and 712 are capable of communication via beacons, exemplarily depicted using dotted lines with the communication module 308 (not shown in the representation 700) included within the head portion 204 of the device 150. In at least one example embodiment, the beacon may include information related to UUID and motion data for the corresponding exercise machine.

In some embodiments, the device 150 may get exposed to huge amount of advertising data from all the beacons. This chaotic situation sometimes results in disregarding the respective beacon from the desired exercise machine. To overcome this problem, the device 150 may be configured to correlate/compare the respective beacons received from the exercise machines with the workout motion data of the user to identify which beacon should be accept and processed.

Since, the beacons contain the exercise machine identifying information it allows the device 150 to identify the exercise machine correctly. As shown by the dotted line 714, the device 150 may identify the exercise machine 702 as being used by a user based on the correlation of motion data and the corresponding beacon. Additionally, proximity of the beacons may also be used to verify the match and accordingly identify the exercise machines. In an embodiment, an accelerometer may also be added with the Bluetooth beacon. The motion data detected by the accelerometer may be added to the beacon data representatively by changing the advertising frequency of the beacons and/or by adding a separate data packet for the motion data. This may further assist in identification of the direction of the movement of the weights.

Figure 8:
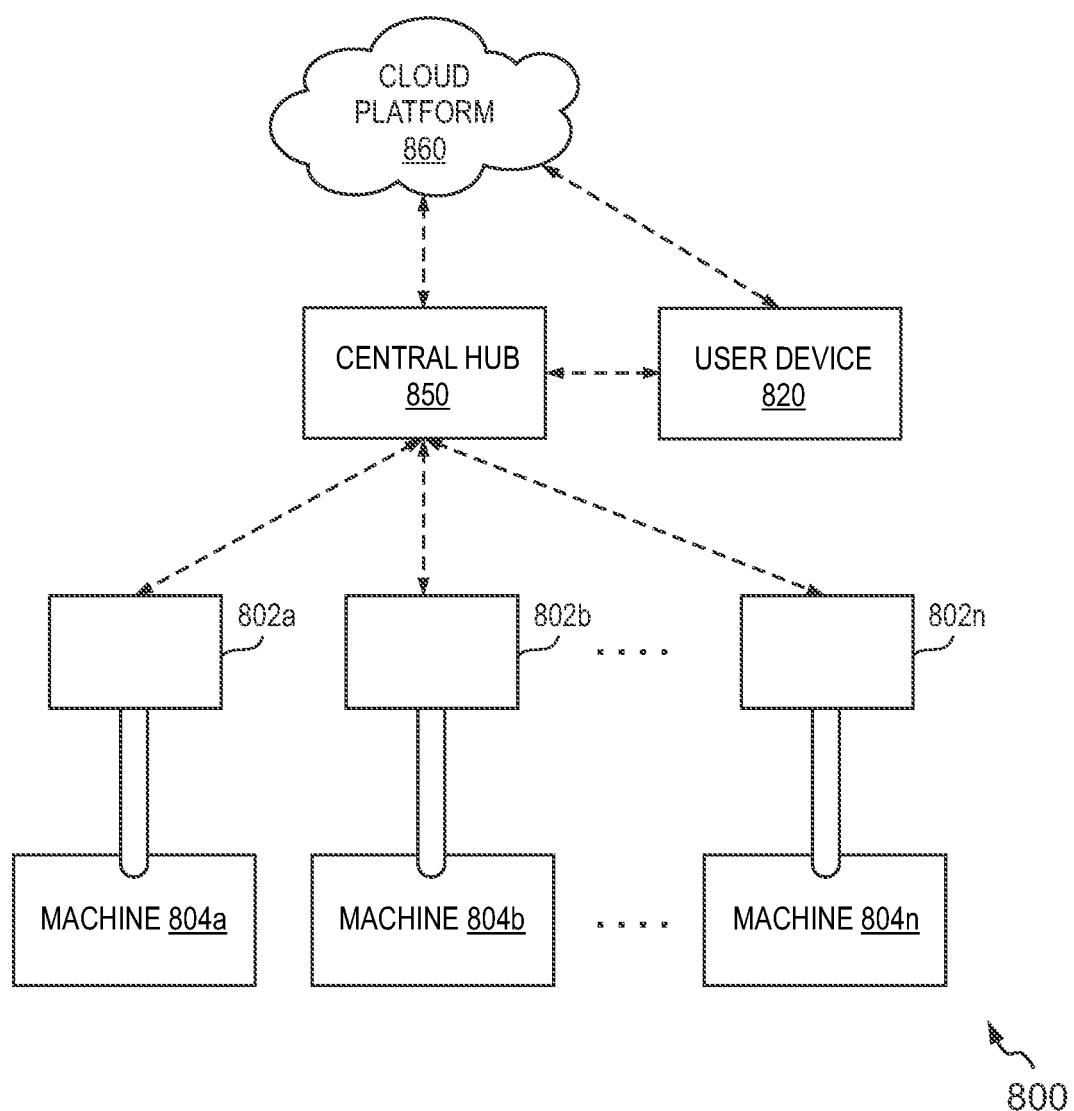
FIG. 8 is a representation showing a plurality of devices communicating with a central hub for logging exercise data, in accordance with an example embodiment of the invention.

FIG. 8 is a representation 800 showing a plurality of devices communicating with a central hub 850 for logging exercise data, in accordance with an example embodiment of the invention. In an example scenario, a gym owner may deploy a plurality of devices, such as the device 150, to log exercise data for each of the weight training machines present in the gym to assist the gym users in conveniently recording exercise data, thereby leading to better workout sessions and enhanced user experiences.

Accordingly, the representation 800 depicts a plurality of devices 802a, 802b to 802n engaged with exercise machines 804a, 804b to 804n, respectively. The devices 802a-n may be configured to communicate over a communication network with a central hub 850. In an embodiment, the central hub 850 may correspond to a Bluetooth enabled or a Wi-Fi enabled communication device capable of receiving data from the plurality of devices 802a-n and transmitting the same to the user device 820 or to a remote server (for example, a cloud platform 860) for further computations. Further, all the users of the gym may be identified using RFID tags which the users can use to 'check into' different weight training machines 802a-n, i.e. the RFID tags may be scanned and processed by the device attached to a machine and the same can be transferred to the cloud platform 860 via the central hub 850 to identify the users and to store/retrieve the exercise data logs associated with the users. In an example embodiment, a user may own the device (such as the device 802a) and use it for automatically logging his/her workout data while exercising on any of the machines 804a-n present in the gym and may connect to the central hub 850 e.g. via Bluetooth or Wi-Fi to send the corresponding exercise data to the respective user device 820.

Figure 9A:
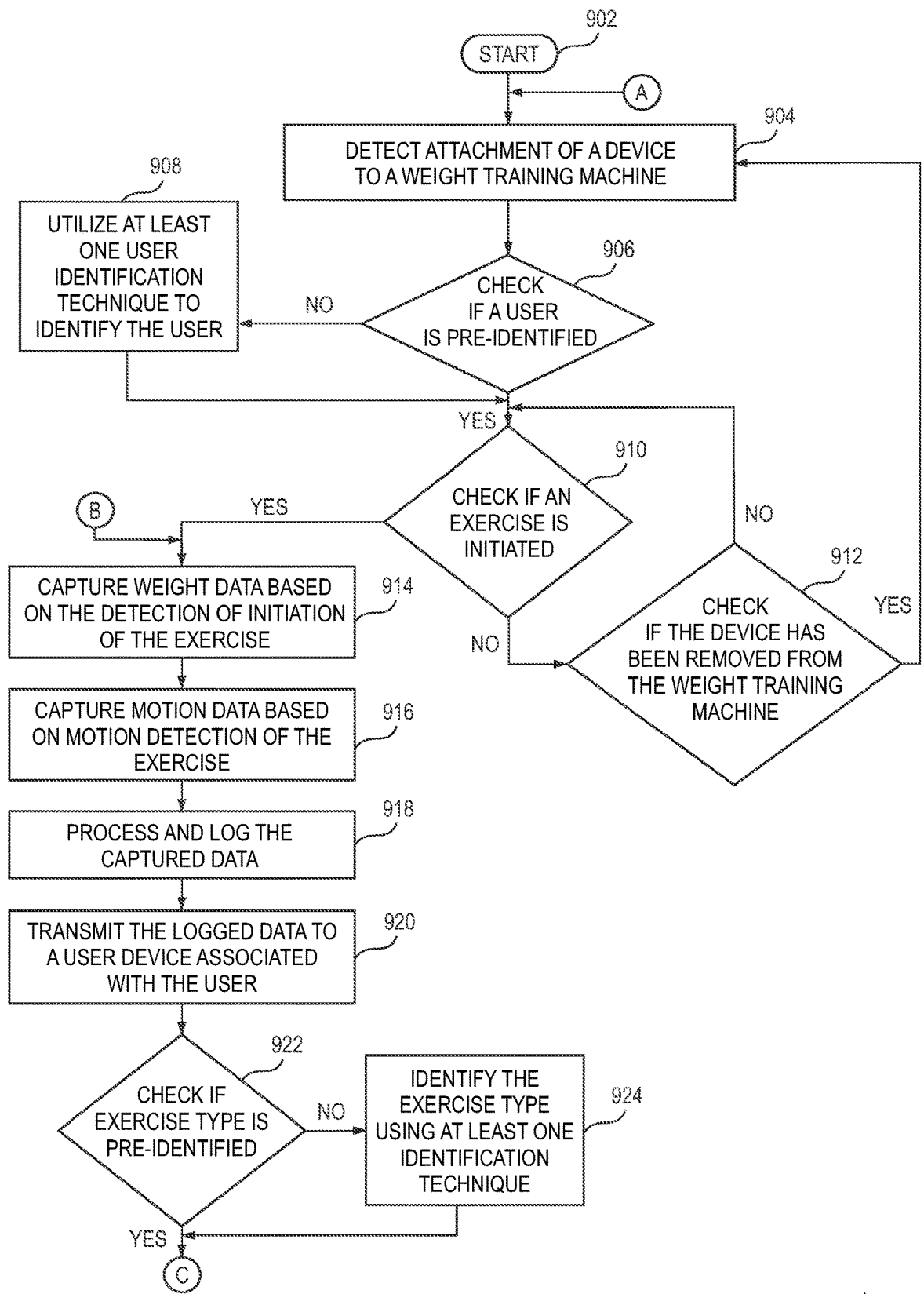
FIGS. 9A and 9B illustrate an example flow diagram of a method for logging exercise data, in accordance with an example embodiment of the invention.
Figure 9B:
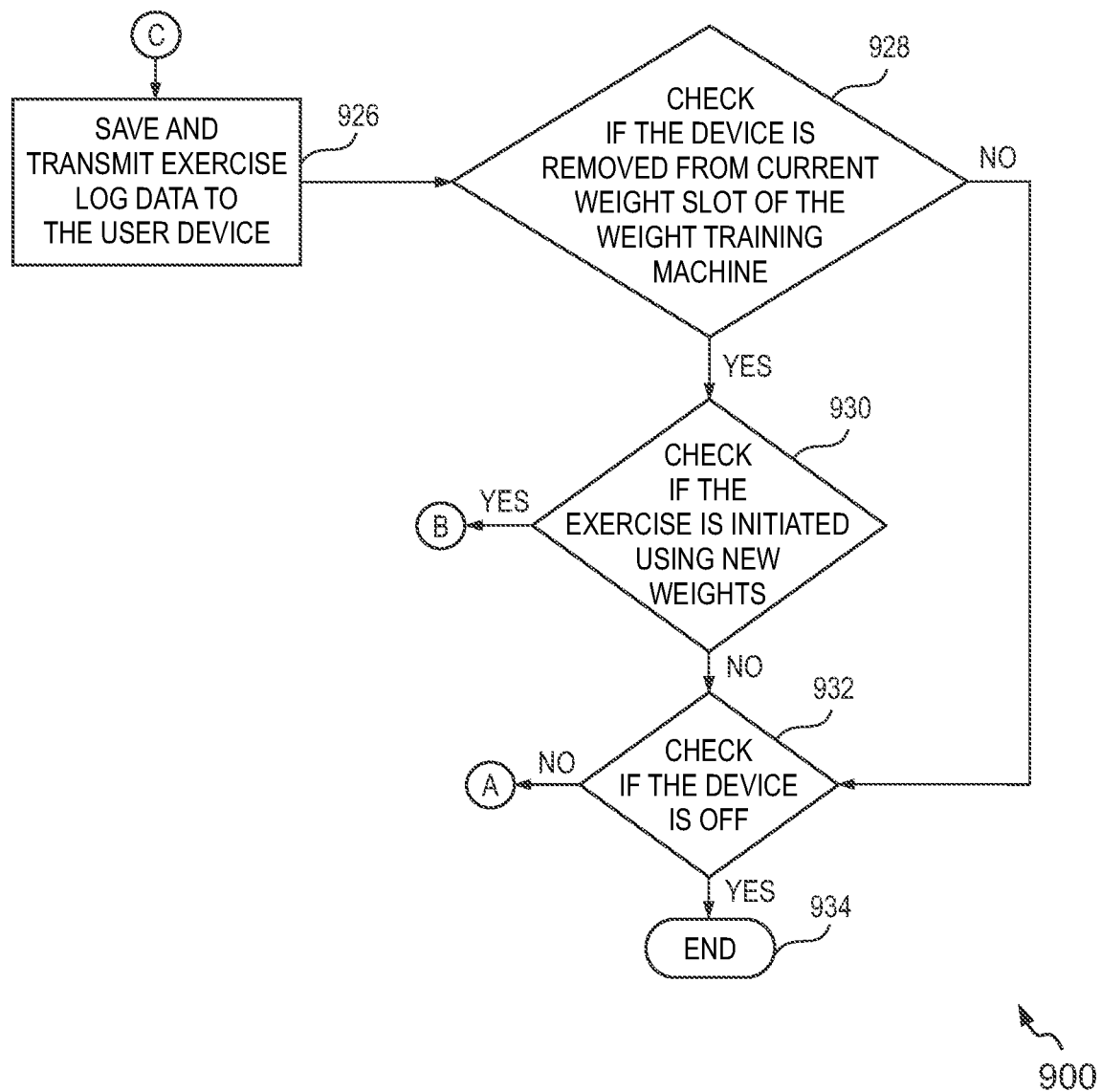

FIGS. 9A and 9B illustrate an example flow diagram of a method 900 for logging exercise data, in accordance with an example embodiment of the invention. The various steps and/or operations of the flow diagram, and combinations of steps/operations in the flow diagram, may be implemented by, for example, hardware, firmware, a processor, circuitry and/or by the device 150 of the present technology and/or by a different device associated with the execution of software that includes one or more computer program instructions. The method 900 starts at 902.

At 904, attachment of a device, such as the device 150, to a weight-training machine is detected. In an embodiment, the device may be turned on to receive power from a power module (such as the power module 310) to start functioning before attaching to the weight-training machine. In other embodiments, the device may automatically turn on the power based on the detection of its attachment to the machine. Alternatively, a motion-based charger may be added to the device to run it.

At 906, it is checked if a user is pre-identified. In an embodiment, the user may create a user account using the UI of a personal computing device and link the user account with the device to facilitate user identification. In some embodiments, the user account may include user image and/or biometric information, which may facilitate user identification.

If the user is not identified at 906, then at 908, at least one user identification technique is utilized to identify the user. If the user is not pre-identified as explained with reference to the previous step, at least one user identification technique such as but not limited to, using the camera integrated with the device or by pairing the user device with the device may be utilized to facilitate user identification.

If the user is identified at 906, then at 910, it is checked if an exercise is initiated. In an embodiment, detection of exercise initiation may be achieved based on sensing of motion by the motion sensor module (such as the motion sensor module 302) of the device.

If the exercise is not initiated at the 910, then at 912, it is checked if the device has been removed from the weight-training machine. If the device has been removed from the weight-training machine, the process restarts from 904. Further, if the device has not been removed from the weight-training machine, then 910 is repeated to check if the exercise has been initiated.

If the initiation of the exercise is detected at 910, then at 914, weight data is captured based on the detection of initiation of the exercise. In an embodiment, the camera included in the weight sensor module of the device may capture visual information (for example, images/video) of the weight labels to facilitate capture of the weight data. At 916, motion data is captured based on motion detection of the exercise.

At 918, the captured data (i.e. captured weight data and motion data, from 914 and 916, respectively) is processed and logged. An analysis module, such as the analysis module 306 of the device 150, may be configured to process the captured data as explained with reference to FIG. 3A.

At 920, the logged data is transmitted to a user device associated with the user. In an embodiment, the device may be configured to send the stored data to the user device using a communication module, such as the communication module 308 of the device 150.

At 922, it is checked if exercise type is pre-identified. In an embodiment, the user may enter a type of exercise into the mobile application associated with the device using a mobile phone or a laptop computer. For example, the user may enter "sit-ups" as the exercise type. Alternatively, the user may pre-select an exercise form the type of exercises displayed on the display screen of the device.

If the exercise type is not pre-identified at 922, then at 924, the exercise type is identified using at least one identification technique. Identification techniques such as analyzing the range of motion of the exercise and using the analysis to determine type of exercise may be employed. Further, the range of motion may be correlated with the beacons emitted by the exercise machine to accurately determine the type of exercise.

At 926, exercise log data is saved and transmitted to the user device based on the identification of the exercise type. The exercise log data may include additional information such as identification of the exercise type and machine type being used by the user for the current set of the workout.

At 928, it is checked if the device is removed from current weight slot of the weight-training machine. The analysis module may be configured to detect a termination of the range of motion of the user.

If the device is not removed from current weight slot of the weight training machine, at 932, it is further checked if the device is off (i.e. powered off).

At 930, it is checked if the exercise is initiated using new weights based on the detection of movement of the device at 928. If the exercise is started, the weight data is captured by redirecting the method flow to 914. Using the operations described in 910, it is determined if the user initiated another set of the exercise using the new weights. Similarly exercise log data associated with the new set of the exercise may be stored on the device or may be sent to the user device. If the exercise is not yet started, at 932, it is checked if the device is off.

If the device is not powered off (i.e. in an active state), the method 900 is redirected to 904. If the device is powered off, the method 900 ends at 934.

Figure 10:
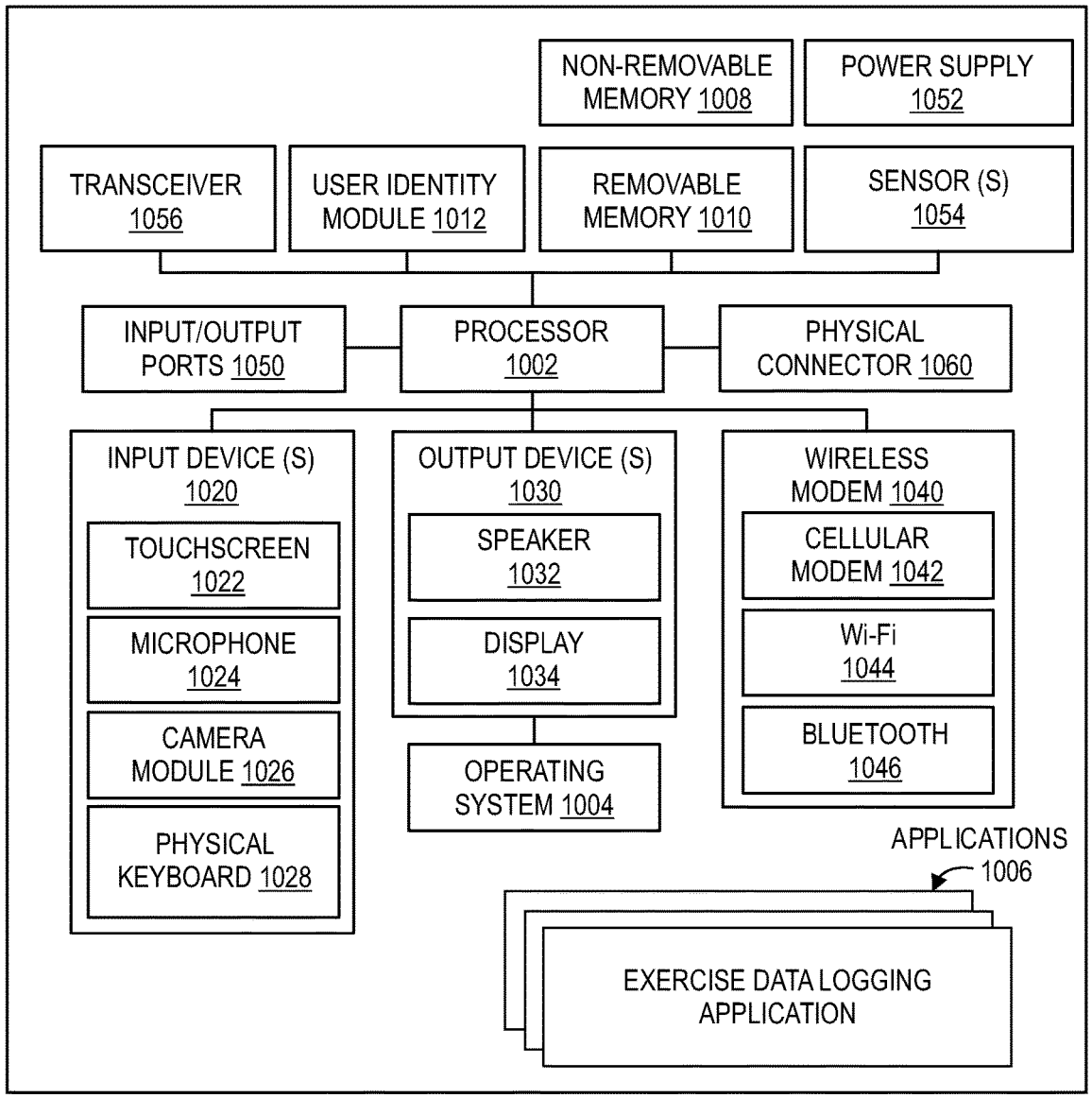
FIG. 10 shows an electronic device capable of facilitating implementation of the various embodiments of the present invention.

FIG. 10 shows an electronic device 1000 capable of facilitating implementation of the various embodiments of the present invention. In an embodiment, the implementation of various operations performed by the device 150 may be facilitated using a fitness tracking application in an electronic device, such as the electronic device 1000. For example, the electronic device 1000 may correspond to an electronic device associated with a user. The electronic device 1000 is depicted to include one or more applications 1006, including a fitness tracking application, referred to herein as 'exercise data logging application' to facilitate logging of exercise data.

The electronic device 1000 as illustrated and hereinafter described is merely illustrative of one type of device and should not be taken to limit the scope of the embodiments. As such, it should be appreciated that at least some of the components described below about that the electronic device 1000 may be optional and thus in an example embodiment may include more, less or different components than those described about the example embodiment of the FIG. 10. As such, among other examples, that the electronic device 1000 could be any of a mobile electronic device, for example, cellular phones, tablet computers, laptops, mobile computers, personal digital assistants (PDAs), mobile televisions, mobile digital assistants, or any combination of the, and other types of communication or multimedia devices.

The illustrated electronic device 1000 includes a controller or a processor 1002 (e.g., a signal processor, microprocessor, ASIC, or other control and processing logic circuitry) for performing such tasks as signal coding, data processing, image processing, input/output processing, power control, and/or other functions. An operating system 1004 controls the allocation and usage of the components of the electronic device 1000 and support for one or more applications programs (see, applications 1006), such as exercise data logging application that implements one or more of the innovative features described herein. In addition to exercise data logging application, the applications 1006 may include common mobile computing applications (e.g., telephony applications, email applications, calendars, contact managers, web browsers, messaging applications) or any other computing application. The exercise data logging application, in at least one example embodiment, may be configured to provide the logic to device 150 for facilitating logging of exercise data, as explained with reference to FIGS. 1 to 8. Further, the exercise data logging application may be configured to display one or more UIs for showing the logged exercise data to the user. The exercise data logging application may also contain predictive algorithms, which use the data to predict workout parameters such as exercise type based on motion profiles. It may also be used to predict user behavior and accordingly provide user feedback to help the users reach their goals and/or help them perform their workout correctly by way of for example, guided live or recorded workout session videos.

The illustrated electronic device 1000 includes one or more memory components, for example, a non-removable memory 1008 and/or removable memory 1010. The non-removable memory 1008 and/or removable memory 1010 may be collectively known as database in an embodiment. The non-removable memory 1008 can include RAM, ROM, flash memory, a hard disk, or other well-known memory storage technologies. The removable memory 1010 can include flash memory, smart cards, or a Subscriber Identity Module (SIM). The one or more memory components can be used for storing data and/or code for running the operating system 1004 and the applications 1006.

The electronic device 1000 can support one or more input devices 1020 and one or more output devices 1030. The input devices 1020 and the output devices 1030 configure the input/output (I/O) module for the electronic device 1000. Examples of the input devices 1020 may include, but are not limited to, a touch screen/a display screen 1022 (e.g., capable of capturing finger tap inputs, finger gesture inputs, multi-finger tap inputs, multi-finger gesture inputs, or keystroke inputs from a virtual keyboard or keypad), a microphone 1024 (e.g., capable of capturing voice input), a camera module 1026 (e.g., capable of capturing still picture images and/or video images) and a physical keyboard 1028. Examples of the output devices 1030 may include, but are not limited to a speaker 1032 and a display 1034. Other possible output devices can include piezoelectric or other haptic output devices. Some devices can serve more than one input/output function. For example, the touch screen 1022 and the display 1034 can be combined into a single input/output device.

A wireless modem 1040 can be coupled to one or more antennas (not shown in the FIG. 10) and can support two-way communications between the processor 1002 and external devices, as is well understood in the art. The wireless modem 1040 is shown generically and can include, for example, a cellular modem 1042 for communicating at long range with the mobile communication network, a Wi-Fi compatible modem 1044 for communicating at short range with an external Bluetooth-equipped device or a local wireless data network or router, and/or a Bluetooth-compatible modem 1046. The wireless modem 1040 is typically configured for communication with one or more cellular networks, such as a GSM network for data and voice communications within a single cellular network, between cellular networks, or between the electronic device 1000 and a public switched telephone network (PSTN). The wireless modem 1040 may in at least one example embodiment configure the communication module of the electronic device 1000.

The electronic device 1000 can further include one or more input/output ports 1050, a power supply 1052, one or more sensors 1054 for example, an accelerometer, a gyroscope, a compass, or an infrared proximity sensor for detecting the orientation or motion of the electronic device 1000, a transceiver 1056 (for wirelessly transmitting analog or digital signals) and/or a physical connector 1060, which can be a USB port, IEEE 1294 (FireWire) port, and/or RS-232 port. The illustrated components are not required or all-inclusive, as any of the components shown can be deleted and other components can be added.

Various example embodiments offer, among other benefits, techniques for or improved data logging of workout sessions. Automatic logging of workout data such as weights used, type of machine, number of repetitions per set of a workout session, the changes made to the amount of weights lifted per set per workout session, and the like, removes the need of manually maintaining the records, which is quite tedious. Further, the data logs may also include data generated from analysis of weight/motion data, such as for example data such as calories burned, maximum heart rate, rest time between two sets, distance covered (if the workout type is running), time spent and the like. Moreover, the data logs may include suggestions for improving the workout session of the user. For example, a body fat composition may be calculated by the analysis module 306 and may be provided as feedback to the user using the UI of the user device. The body fat composition may include fat percentage and muscle percentage of the user's body which may provide the user with clues to modify workout types/intensity and the like if needed.

Further, device of the present invention can be easily integrated with different workout machine types without the need for complex installation process. This saves the hassle of replacing machines and installation of complex hardware. As the conventional weight stack pin is already a part and parcel of a user's workout sessions, the user does not need to develop a special learning curve to use the device (which is structurally like the conventional weight stack pin) and therefore the device easily fits in the user's routine of working-out, thereby making the whole process seamless. Further, the device can be used by gym trainers for recording their client's workout related data. The device can be used by athletes and sports teams to understand and improve their performances. Also, the device can be used by gym owners who want to provide workout data to their users. The ability to remove the head portion of the device and attach it to different conventional pins or to different exercise equipments provides additional flexibility to the users. Moreover, real time feedback from the device using light variations or vibrations or notifications being sent on user's device helps the user to modify the workout in real time. For example, if the user has been using same amount of the weights for continuous two sets of a workout session, the user may be prompted in real time to add some more weight in the third set to get extra benefits from that workout session.

Although the invention has been described with reference to specific exemplary embodiments, it is noted that various modifications and changes may be made to these embodiments without departing from the broad spirit and scope of the invention. For example, the various operations, blocks, etc., described herein may be enabled and operated using hardware circuitry (for example, complementary metal oxide semiconductor (CMOS) based logic circuitry), firmware, software and/or any combination of hardware, firmware, and/or software (for example, embodied in a machine-readable medium). For example, the devices and methods may be embodied using transistors, logic gates, and electrical circuits (for example, application specific integrated circuit (ASIC) circuitry and/or in Digital Signal Processor (DSP) circuitry).

Particularly, the device 150 and its various components, such as the motion sensor module 302, weight sensor module 304, the analysis module 306, the communication module 308, the power module 310 may be enabled using software and/or using transistors, logic gates, and electrical circuits (for example, integrated circuit circuitry such as ASIC circuitry). Various embodiments of the invention may include one or more computer programs stored or otherwise embodied on a computer-readable medium, wherein the computer programs are configured to cause a processor or computer to perform one or more operations (for example, operations explained herein with reference to FIGS. 9A and 9B). A computer-readable medium storing, embodying, or encoded with a computer program, or similar language, may be embodied as a tangible data storage device storing one or more software programs that are configured to cause a processor or computer to perform one or more operations. Such operations may be, for example, any of the steps or operations described herein. In some embodiments, the computer programs may be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), DVD (Digital Versatile Disc), BD (BLU-RAY® Disc), and semiconductor memories (such as mask ROM, PROM (programmable ROM), EPROM (erasable PROM), flash memory, RAM (random access memory), etc.). Additionally, a tangible data storage device may be embodied as one or more volatile memory devices, one or more non-volatile memory devices, and/or a combination of one or more volatile memory devices and non-volatile memory devices. In some embodiments, the computer programs may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

The foregoing descriptions of specific embodiments of the present disclosure have been presented for purposes of illustration and description. They are not intended to be exhaustive or to limit the present disclosure to the precise forms disclosed, and obviously many modifications and variations are possible considering the above teaching. The exemplary embodiment was chosen and described to best explain the principles of the present disclosure and its practical application, to thereby enable others skilled in the art to best utilize the present disclosure and various embodiments with various modifications as are suited to the use contemplated.

The embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A device for logging exercise data, the device comprising:
    a body for engaging with an exercise machine, the body having:
        a head with a first center line; and
        a shaft extending from the head, the shaft having a second center line, the first center line is offset from the second center line;
    an electrical system with a power source incorporated into the body and configured to record data;
    an image sensor incorporated into the body and configured to capture an image, the image sensor is secured to the head and oriented to capture images of the exercise machine; and
    a motion sensor incorporated into the body and configured to detect movement;
    wherein the image sensor determines a weight load associated with the exercise machine by capturing images of the exercise machine;
    wherein the motion sensor detects and records a number of repetitions of movement; and
    wherein the device creates an exercise log associated with a user's workout.

2. The device of claim 1, further comprising:
    a communication module incorporated into the electrical system and configured to wirelessly communicate with one or more electronic devices;
    wherein the communication module is configured to transmit the exercise log to the one or more electronic devices.

3. The device of claim 2, wherein the communication module includes a signaling device capable of transmitting beacons.

4. The device of claim 1,
    wherein the shaft is secured to the weight load of the exercise machine.

5. The device of claim 4, wherein the head is detachably engaged with the shaft.

6. The device of claim 1, wherein the image sensor is a camera.

7. The device of claim 1, wherein the motion sensor is selected from one of:
    an accelerometer;
    a gyroscope;
    a magnetometer; and
    a vibration sensor.

8. The device of claim 1, further comprising:
    a motion based charging unit incorporated into the body and configured to convert motion of the exercise machine to generate current.

9. The device of claim 1, wherein the motion sensor is configured to detect presence of motion and thereafter activate weight sensing operation via the image sensor for facilitating logging of exercise data.

10. The device of claim 1, wherein the electrical system further includes:
    an analysis module configured to perform logical operations on data received from the motion sensor and the image sensor to determine weights lifted by the user.

11. The device of claim 1, wherein the image sensor is configured to detect an identity of the user via facial recognition.

12. A workout system, comprising:
    an exercise machine, having:
        one or more weights;
    a first device having a body configured to engage with the exercise machine,
    the body having:
        a head with a first center line; and
        a shaft extending from the head, the shaft having a second center line, the first center line is offset from the second center line;
    the first device having:
        an electrical system with a power source and configured to receive and record data;
        an image sensor to capture an image, the image sensor is secured to the head and oriented to capture images of the exercise machine; and
        a motion sensor configured to detect movement;
    wherein the image determines a weight amount being manipulated by a user;
    wherein the motion sensor detects and records a number of repetitions of movement; and
    wherein the first device logs exercise data associated with the user using the exercise machine.

13. The system of claim 12, wherein the first device further comprises:
    a communication configured to wirelessly communicate with and transmit exercise data to one or more user devices.

14. The system of claim 13, wherein the one or more user devices is a smart phone.

15. The system of claim 13, further comprising:
    a cloud platform configured to wirelessly communicate with the one or more user devices and the first device;
    wherein data is processed remotely via the cloud platform and retrieved later by the user via the one or more user devices.

16. The system of claim 12, further comprising:
    one or more other exercise machines each having a signaling device capable of transmitting beacons and a unique identifier associated therewith;

wherein the first device is configured to recognize each of the one or more other exercise machines via communication with the signaling device and the unique identifier.

17. The system of claim 12, further comprising:

a second device configured to collect exercise data; and a central computing hub configured to wirelessly communicate with the first device and the second device to create a log associated with the first device and the second device.

* * * * *